United States Patent [19]

Aldrich et al.

[11] Patent Number: 4,981,981

[45] Date of Patent: Jan. 1, 1991

[54] SESQUITERPENE EPOXIDES AND PROCESS FOR THEIR PREPARATION

[75] Inventors: Jeffrey R. Aldrich, College Park; James E. Oliver, Laurel, both of Md.; Kyriacos C. Nicolaou, Havertown; Brian E. Marron, Philadelphia, both of Pa.

[73] Assignees: The United States of America as represented by the Secretary of Agriculture, Washington, D.C.; The Trustees of the University of Pennsylvania, Philadelphia, Pa.

[21] Appl. No.: 168,047

[22] Filed: Mar. 14, 1988

[51] Int. Cl.$^5$ ............................................ C07D 303/06
[52] U.S. Cl. ..................................... 549/546; 549/523
[58] Field of Search ............................... 549/546, 523

[56] References Cited

PUBLICATIONS

Ishiwatari, "Chemical Abstracts", vol. 82, 1975, Col. 152415v.
Lockwood, et al., "Ann. Entomol. Soc. Am.", vol. 78(4), 1985, pp. 474-479.
Aldrich et al., "Chemical Abstracts", vol. 108, 1988, col. 108:72532W.
W. C. Mitchell and R. F. L. Mau, "Response of the Female Southern Green Stink Bug and Its Parasite, *Trichopoda Pennipes* to Male Stink Bug Pheromones", *Journal of Economic Entomology*, 64:856-859 (1971).
V. E. Harris and J. W. Todd, "Male-Mediated Aggregation of Male, Female and 5th-Instar Southern Green Stink Bugs and Concomitant Attraction of a Tachinid Parasite, *Trichopoda pennipes*", *Ent. Exp. & Appl.* 27:117-126 (1980).
C. Pavis, "Aspects de la Communication Pheromonale et de le Sensibilite Olfactive Chez un Heteroptere Pentatomidae: *Nezra viridula* (L.)", *These de 3 Cycle de Biologe animale*, Universite de Paris-Sud Centre d'Orsay (1986).
C. Pavis and C. Malosse, "Mise en evidence d'u attractif sexual produit par les males de Nezara viridula (L.) (Heteroptera: Pentatomidae", *C. R. Acad. Sc. Paris* Series III 7:273-276 (1986).
M. Borges, C. P. Jepson, and P. E. Howse, "Long-range Mate Location and Close-range Courtship Behavior of the Green Stink Bug, *Nezara viridula* and Its Mediation by Sex Pheromones", *Entomol. Exp. Appl.* 44:205-212 (1987).
R. Baker, M. Borges, N. G. Cooke, and R. H. Herbert, "Identification and Synthesis of (z)-(1'S, 3'R, 4'S)(−)-2-(3', 4'-Epoxy-4'-methylcyclohexyl)-6-methylhepta-2,5-diene, the Sex Pheromone of the Southern Green Stinkbug, *Nezara viridula* (L)", *J. Chem. Soc. Chem. Commun.* 1987:414-416.
F. Delay and G. Ohloff, "Synthesis of (R)-and (S)-p--Mentha-1,8-dien-4-ols from (R)-Limonene", *Helvetica Chemica Acta* 62:2168-2173 (1979).

*Primary Examiner*—Glennon H. Hollrah
*Assistant Examiner*—James H. Turnipseed
*Attorney, Agent, or Firm*—M. Howard Silverstein; John D. Fado; Margaret A. Connor

[57] ABSTRACT

The novel sesquiterpene epoxides trans-(Z)-1-methyl-4-(1,5-dimethyl-1,4-hexadienyl)-1,2-epoxycyclohexane and cis-(z)-1-methyl-4-(1,5-dimethyl-1,4-hexadienyl)-1,2-expoxycyclohexane have been isolated from *N. viridula* adult males, and have been successfully synthesized. The compounds are useful for the production of synthetic sex attractants for *N. viridula* and its parasitoids.

7 Claims, 6 Drawing Sheets

R-cis

R-trans

S-cis

S-trans

Step 1

Step 2

Step 3

Step 4

Step 5

Step 6

Step 7

4,981,981

SESQUITERPENE EPOXIDES AND PROCESS FOR THEIR PREPARATION

BACKGROUND OF THE INVENTION

1. Field of the Invention

This invention relates to the provision of novel sesquiterpene epoxides and ways of preparing and using the novel compounds.

2. Description of the Art

The stink bug *Nezara viridula* (Hemiptera: Heteroptera: Pentatomidae) is native to the Ethiopian region, but has been spread by commerce to every continent and many islands between 45° north and south latitudes. Both the adult and immature bugs feed on developing fruits and seeds by sucking sap or oil through hypodermic-like mouthparts. Thus, the insects directly damage the most valuable portion of a crop, yet the damage is not as obvious as for insects eating foliage. Feeding by *N. viridula* also indirectly reduces yield and seed quality by transmission of diseases.

Nezara attacks a wide range of fruit, field crops, vegetables, and nut crops. In the United States, *N. viridula* (called the southern green stink bug) is a major pest of soybean south of a line extending from Texas in the west through southern Arkansas to Virginia in the east. The insect (called the green vegetable bug in some other countries) is also a major and frequent pest of soybean in Central and South America, China, Korea, Japan, India, Australia, New Zealand, and Africa. In the U.S., the bug is an unpredictable, occasional pest of pecans and some vegetables, particularly tomatoes. The southern green stink bug has recently extended its range to California where it has already become a pest of tomatoes. In Japan and other rice-producing countries, *N. viridula* can be a serious pest of this crop.

Nezara adults are strong fliers and frequently migrate to different fields of the same or other maturing crops. In the absence of food or with the onset of winter in warm temperate regions, adults are able to hibernate and resume attack the following season. In many parts of the world where *N. viridula* is established there is a scarcity of effective parasites and predators despite efforts to introduce these biocontrol agents. Their initially inconspicuous feeding damage, combined with a facility for migration and lack of natural enemies, make *N. viridula* an especially difficult pest to control.

One control tactic that is somewhat effective in reducing Nezara infestation of soybean is the trap crop technique. This method entails planting small acreages of soybean 10–14 days earlier than the main crop. The early maturing soybean attracts migrating Nezara adults which mate and reproduce in the trap crop. Maturing second generation bugs are then destroyed by insecticide application. This approach is economical because relatively small areas are sprayed, and minimizes environmental pollution and destruction of natural enemies. However, incomplete attraction of adult bugs and the ability of the adults to evade insecticide treatment are serious drawbacks to this control strategy.

A chemical attractant, such as the synthetic sex pheromones available for many kinds of moths, would be a valuable tool for monitoring and manipulating Nezara populations. Field tests using caged bugs have demonstrated that *N. viridula* adult males release a pheromone attractive to conspecific male and female adults and fifth-instar nymphs, and that *Trichopoda pennipes* (Diptera: Tachinidae), a fly that is parasitic on *N. viridula*, uses the pheromone as a kairomone (Mitchell and Mau, *Journal of Economic Entomology* 64: 856–859 (1971); Harris and Todd, *Entomol. Exp. & Appl.* 27: 117–126 (1980)). However, attempts to identify the pheromone have met with only limited success. Pavis (*These de 3 Cycle de Biologie animale*, Universite de Paris-Sud Centre d'Orsay (1986)) and Pavis and Malosse (C. R. Acad. Sc. Paris Series III, 7:273–276 (1986)) reported the presence of two pairs of isomers having molecular weights (MW) of 220 and 224 in two fractions of a hexane extract from the ventral abdominal integument of mature males of European *N. viridula*. The fraction containing the 224 MW compounds reportedly was attractive to *N. viridula* females, and the fraction containing the 220 MW compounds reportedly served as a mating stimulant. The four compounds were tentatively characterized as cyclic sesquiterpenes, but the compounds were not individually isolated and the structures were not identified.

SUMMARY OF THE INVENTION

We have for the first time obtained in pure or substantially pure form the novel sesquiterpene epoxides trans-(Z)-1-methyl-4-(1,5-dimethyl-1,4-hexadienyl)-1,2-epoxycyclohexane, and cis-(Z)-1-methyl-4-(1,5-dimethyl-1,4-hexadienyl)-1,2-epoxycyclohexane. These compounds have been isolated from *N. viridula* males and have also been successfully synthesized. Traps baited with extracts of male *N. viridula* which contained these compounds as major components, caught female and male *N. viridula* and *T. pennipes*, indicating the usefulness of these compounds in the production of synthetic sex attractants for *N. viridula* and its parasitoids.

The trans and cis compounds have a piney, woody odor and are useful as perfume or flavor components.

Additional potential uses of the compounds of the invention are as reference compounds for natural product chemistry and in the pharmaceutical industry as precursors for new pharmaceuticals.

In accordance with this discovery, it is an object of the invention to provide novel sesquiterpene epoxides useful in the preparation of synthetic sex attractants for *N. viridula* and its parasitoids, as odor or flavoring additives, as reference compounds and as pharmaceutical precursors.

A further object of the invention is to provide a method to synthesize the novel compounds.

Other objects and advantages of the invention will become readily apparent from the ensuing description.

DETAILED DESCRIPTION OF THE INVENTION

The novel sesquiterpene epoxides of the invention are the first pheromonal compounds identified for a plant-feeding insect in the order Hemiptera, suborder Heteroptera (ca. 35,000 species worldwide). They are characterized by the structural formulas shown in FIG. 1. The trans-(Z)-1-methyl-4-(1,5-dimethyl-1,4-hexadienyl)-1,2-epoxycyclohexane is illustrated by number 8 and the cis-(Z)-1-methyl-4-(1,5-dimethyl-1,4-hexadienyl)-1,2-epoxycyclohexane is illustrated by number 9. The compounds are epoxides of 1-methyl-4-(1,5-dimethyl-(Z)-1,4-hexadienyl)-cyclohexene [(Z)-α-bisabolene], and the trans and cis compounds of the invention are hereinafter referred to as trans-(Z)-α-bisabolene epoxide and cis-(Z)-α-bisabolene, expoxide respectively. As used in the specification and the claims, the phrase "pure or substantially pure" means that with regards to the synthetic material, the novel compounds of the invention have purity equal to or greater than that obtained when synthesized in accordance to the procedure outlined in Example 2, and in cases where the compounds have been obtained from *N. viridula* volatiles, purity is equal to or greater than that obtained in accordance with the isolation procedure outlined in Example 1.

ISOLATION OF THE COMPOUNDS

Figure 2:
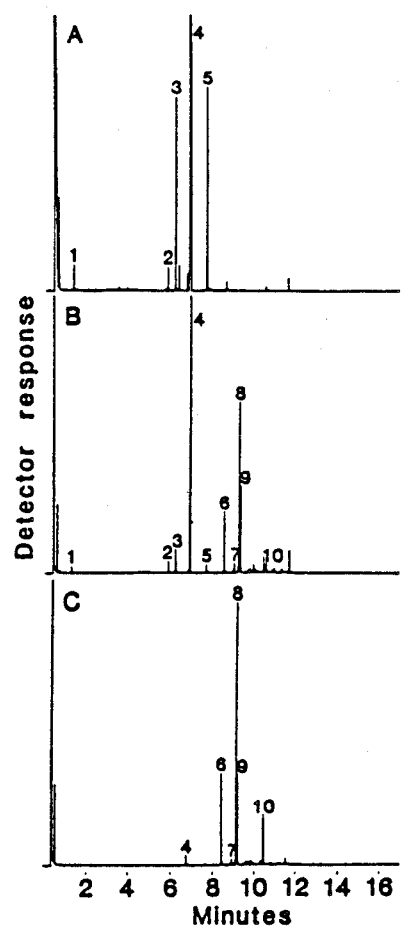
FIG. 2 show gas chromatograms of airborne-trapped volatiles from groups of 25 sexually mature *N. viridula* virgin males. A: Metathoracic scent gland secretion. B: Males loaded without scent gland emission, but with one male dying during trapping. C: Males loaded without emitting scent gland secretion and with none dying.

The novel compounds were isolated from the volatiles of *N. viridula* as described in detail below in Example 1. Isolation of the novel compounds of the invention from *N. viridula* presented problems of unusual difficulty. One problem is that these insects are so-called stink bugs which have defensive glands in their metathorax that confound the task of isolating pheromone compounds from extracts. The bugs secrete large amounts of defensive secretion that can contaminate extracts of the insects and inhibit release of the true pheromone in airborne-trapping devices. This is illustrated in FIG. 2 which shows samples of *N. viridula* volatiles analyzed by gas chromatography. When the odor of the metathoracic scent gland secretion was detected at the start of a male *N. viridula* airborne-trapping run, compounds 6–10 were usually greatly reduced in absolute abundance and the constituents of the metathoracic gland secretion (compounds 1–5) were abundant (FIG. 2A). Similarly, if one or more of the males died during an airborne-trapping run, the constituents of the metathoracic scent gland secretion appeared in the sample and compounds 6–10 were more or less reduced in abundance depending on when the males died (FIG. 2B). When mature males were coaxed into the airborne-trapping apparatus without causing them to emit their metathoracic scent gland secretion and when none died during trapping, they released predominantly compounds eluting from 8–11 minutes (FIG. 2C).

Another problem is that these insects do not store pheromone in a gland that can be removed from the insect and thus isolation of pheromone from the bugs is difficult. Moreover, a male releases at most only a few micrograms of pheromone per day, thus obtaining sufficient material for isolation and identification is very difficult. Another problem in working on *N. viridula* is that this pest is primarily a tropical insect and no artificial diet is available for the insect. Rearing the insect is difficult because a continuous supply of fresh plant food is required.

IDENTIFICATION OF THE NOVEL COMPOUNDS

The identification of the novel compounds of the invention is described in detail in Example 1, below. Identification of the novel epoxides of the invention also presented problems of unusual difficulty. The trans- and cis-(Z)-α-bisabolene epoxide isomers are chemically very much alike, therefore it is correspondingly difficult to isolate one from the other. Additionally, identification of the novel epoxides was particularly difficult because no precedent for this structure existed. Prior to the invention, these compounds were not known. Further, this is the first time the components of the pheromonal fraction have been identified for a plant-feeding insect in the order Hemiptera, suborder Heteroptera, thus there was no suggestion that the novel compounds of the invention would occur in the pheromonal extract of *N. viridula*. Structural elucidation of unknown chemicals is difficult because limited theoretical basis exists for predicting chemical structure from mass spectroscopic data. The relationships between mass spectral pattern and structure are not well understood theoretically in enough cases to permit structure assignment by theory alone.

In addition to lack of precedent of structure assignment, another difficulty in the identification of the compound was that only limited amounts of the isolated compounds were available. It was necessary to repeatedly isolate 50–500 micrograms of each isomer to obtain nuclear magnetic resonance, infrared, and ultraviolet spectral data. To obtain final elucidation of the of the structures, microchemical ozonolysis and deoxygenation reactions were carried out, as disclosed in detail below.

Added difficulty in the structural determination was that the compounds readily decompose under even mildly acidic conditions. In order to obtain enough of each compound for the various experiments to elucidate structure, a wide-bore capillary GC column was employed from which the isomers were trapped as they eluted. This entailed 20–30 injections onto the GC column in one day to trap one of the isomers, with the opposite isomer being lost in the process. The strongest piece of analytical data proving structure was the deoxygenation reaction whereby it was shown that each epoxide isomer was converted to (Z)-α-bisabolene. Use of this reaction for structural elucidation is a new application of the technique which was originally employed in a synthetic scheme for menthane-type alcohols by Delay and Ohloff, *Helvetica Chimica Acta* 62: 2168–2173 (1979).

Published electron impact mass spectra (EI-MS) matching the spectra for trans-(Z)-α-bisabolene epoxide (compound 8, FIG. 1) and cis-(Z)-α-bisabolene epoxide (compound 9, FIG. 1) could not be found. The similarity of the EI-MS for these two natural products suggested that the compounds were isomers, and their molecular weight (MW)=220 as determined by $NH_3$ chemical ionization mass spectra (CI-MS) indicated they were probably mono-oxygenated sesquiterpenes. Approximately 200 μg of 8 and 9 gas chromatographically trapped together produced a 60 MHz $^1$H-NMR spectrum that was apparently not complicated by the coexistence of two compounds, further suggesting that the compounds were isomers both having the (Z)-configuration. The $CDCl_3$ $^1$H-NMR spectrum of compounds 8 and 9 corresponded to the $^1$H-NMR spectrum of (Z)-α-bisabolene, except that the cyclic olefinic proton signal was shifted upfield and the one methyl group resonance was shifted upfield. The $C_6D_6$ $^1H$-NMR spectrum of compounds 8 and 9 was similar to the $CDCl_3$ $^1H$-NMR spectrum of the compounds, except that the single proton resonance was shifted further upfield. A similar solvent-dependent upfield shift has been observed in the $^1H$-NMR spectra of bisabolene derivatives containing an epoxide group on the ring, and we confirmed this effect on our NMR instrument using a synthetic epoxide of oleic acid. Therefore, we suspected that compounds 8 and 9 were identical to compound 6, but with a C-1,2 epoxide moiety.

To obtain precise elucidation of the compounds, they were deoxygenated and the deoxygenation product (compound 6, FIG. 1) determined. Further, compounds 8 and 9 were ozonated and the products identified (compounds 12 and 13, respectively, FIG. 1).

Although a pair of 224 MW sesquiterpene isomers were reported by Pavis, supra, and Pavis and Malosse, supra, a computer search of the EI-MS recorded for a concentrated pooled sample of our *N. viridula* male airborne samples (ca. 250 insect equivalents) failed to produce a match with either of the EI-MS reported by Pavis, supra, for 224 MW sesquiterpenes from European *N. viridula* males.

SYNTHESIS OF THE COMPOUNDS

Figure 3:
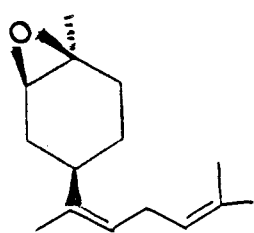
FIG. 3 shows the R-cis, R-trans, S-cis, and S-trans structures of (Z)-1-methyl-4-(1,5-dimethyl-1,4-hexadienyl)-1,2-epoxycyclohexane.
Figure 3:
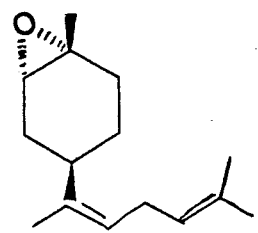
Figure 3:
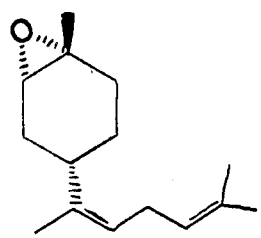
Figure 3:
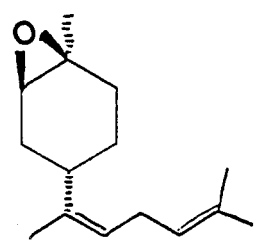

The synthesis of trans-(Z)-α-bisabolene epoxide and cis-(Z)-α-bisabolene epoxide is described in detail in Example 2 below. The (1S,2R,4S)-(−)-enantiomers and the (1R,2S,4R)-(+)-enantiomers of trans- and cis-(Z)-α-bisabolene epoxides were synthesized for verification of structural determinations for the insect-derived compounds. The structures of the four stereoisomers are shown in FIG. 3. Our synthesis starts with either R-(+)-limonene oxide or S-(−)-limonene oxide, each as a mixture of cis- and trans-epoxides in a ca. 1:1 mixture. The use of these starting materials establishes the stereochemistry at C-4 (bisabolene numbering, FIG. 1) as either R or S. The cis and trans mixture of limonene oxide is ozonized, with the ozonide decomposed by triphenylphosphine. The two diastereomers are separable at this stage using gradient elution with flash column chromatography. However, it was found that separation is more easily effected at a later stage in the synthesis. The methyl ketones formed are converted to the volatile terminal acetylene which has a sweet piney odor using a slight modification of the procedure of Negishi et al. (*Journal of Organic Chemistry* 40: 2526 (1980)). The terminal acetylene is acylated with methyl chloroformate after forming the acetylenic anion using n-butyl lithium. The α,β-acetylenic esters are stereoselectively converted to the (Z)-α,β-unsaturated methyl esters using the procedure of E. J. Corey (*Journal of the American Chemical Society* 91: 1851–1852 (1969)). This is the most crucial step as it establishes the Z stereochemistry of the double bond between C-8 and C-10. Only one isomer (all Z no E) is detected. The α,β-unsaturated ester is reduced with diisobutylaluminum hydride to give the allylic alcohol. Conversion of the allylic alcohol to either the allylic chloride or the allylic bromide is carried out using standard procedures. The allylic halide is displaced by the anion formed between 1-bromo-2-methyl propene and t-butyl lithium to yield the desired products in good yields.

The synthesis has the following advantages: it is stereoselective providing only one double bond isomer between C-8 and C-9; the starting material which is inexpensive and commercially available establishes the remaining stereochemistry of the desired products; there are no tedious or difficult separations; it is amenable to large scale production, and the yields range from good to excellent.

The EI-MS and GC-retention times of synthetic trans- and cis-(Z)-epoxides were identical to insect-derived compounds 8 and 9, respectively. In addition, the 500 MHz $^1H$-NMR spectra of isolated 8 and isolated 9 matched the spectra for synthetic 8 and 9, except for the presence of a signal at 0.4 ppm in the insect samples due to methylsilicone contamination from GC column bleed during trapping.

USES OF THE COMPOUNDS

The trans and cis epoxides of the invention find many uses. One important use is for the production of synthetic sex attractants for *N. viridula* and its parasitoids, e.g., *T. pennipes*. For this purpose, the compounds may be used individually or blended together, for example in ratios approximating the ratios which these compounds naturally occur in the various strains of *N. viridula*. For example, the ratio of trans-(Z)-α-bisabolene epoxide to cis-(Z)-α-bisabolene epoxide in the U.S. strain of *N. viridula* from Mississippi is about 2.93±0.05 (mean±standard error of the mean). This determination is based on GC analysis of 176 different airborne-trapped samples from ca. 5,280 laboratory-reared males. Analysis of a U.S. strain of *N. viridula* derived from Florida showed that the amount of cis epoxide in the pheromone volatiles was significantly less. This was the first indication that different geographic populations of Nezara exhibit differing ratios of the isomers. The ratio of the trans to cis isomer for the Japanese strain of *N. virdula* is 1.01±0.10 based on 11 different airbornes of ca. 75 laboratory-reared males. Where other strains of *N. viridula* are to be attracted, the ratio of isomers in the pheromonal extract would be determined as described in detail in Example 1, and a synthetic sex attractant would be prepared containing the so-determined ratio of isomers.

It is envisioned that the synthetic attractants prepared using the novel compounds would be useful in monitoring or controlling *N. viridula* populations and parasitoids when used in conjunction with any type of trap or sex attractant disseminator as known in the art. For this purpose, the sex attractant composition would be applied to a locus of the adults in an amount effective to attract *N. viridula* adults and parasitoids to the bait at a rate significantly higher than the insects are attracted to a nonbaited location.

Another important use of the compounds of the invention is organoleptic compounds for use in food and perfumery industries. The compounds have a piney, woody odor. The cis-(Z)-isomer has a light piney odor with a sweet smell; the trans-(Z)-isomer has a woody, piney odor which is not as sweet as the other isomer. The compounds may be used individually as perfume or flavor components or blended together in various blends to achieve the desired odor. Suggested uses include as an odor component of air fresheners and the like.

Another important use of the compounds is as reference compounds, particularly in the area of natural product chemistry. The availability of synthetic standards would assist in the identification of sesquiterpenoids from other strains of *N. viridula*, other insects, or marine organisms. Also, the compounds may be used as intermediates in the biosynthesis of other cyclic-sesquiterpenoid compounds.

A potential use of the novel compounds is in the development of new antibiotics. Bisabolene derivatives have been found in algae, sponges, corals, and sea slugs (nudibranchs). Several derivatives of α-bisabolene from marine organisms have been found to exhibit antimicrobial activity. The epoxide moiety of the novel compounds of the invention is a reactive center in these molecules that may yield cyano-, thiocyano-, or other derivatives resembling the marine natural products having antibiotic activity. Thus, the novel compounds may be useful for the generation of new pharmaceuticals.

EXAMPLES

The following examples are intended only to further illustrate the invention and are not intended to limit the scope of the invention which is defined by the claims.

Example 1

Isolation of Trans- and Cis-(Z)-α-bisabolene Epoxides. Nezara viridula adults were collected near Stoneville, Miss., and reared in Maryland on sunflower seeds, peanuts, and green beans at 28° C. and 65% relative humidity, on a LD 16:8 hour photoperiodic regime. Samples were collected from groups of 25 virgin adult males or females of known age by coaxing the bugs into a 785 ml glass column and trapping volatiles from the air drawn by vacuum (100 ml/min) over the bugs through 30 mg of activated charcoal for 24 hours. Trapped volatiles were washed from the filter in 200 μl of $CH_2Cl_2$ and stored at −20° C.

Samples of volatiles were analyzed by GC on a bonded methyl silicone column (0.25 μm film, 14 m×0.25 mm ID; "DB-1", J & W Scientific, Rancho Cordova, Calif.) using a Varian 3700 GC with helium as carrier (40 cm/sec), and a temperature program from 45° C. for 2 minutes to 230° C. at 15°/min. The major male-specific terpenoids were trapped in glass capillary tubes jacketted in dry ice as they eluted from a "DB-1" column (15 m×0.53 mm ID) in a Varian 3700 GC equipped with a thermal conductivity detector.

As previously discussed, stink bugs have defensive glands in their metathorax that confound the task of isolating their sex pheromones. When the odor of the metathoracic scent gland secretion was detected at the start of a male N. viridula airborne-trapping run, compounds 6-10 were usually greatly reduced in absolute abundance and the constituents of the metathoracic gland secretion (compounds 1-5) were abundant (FIG. 2A). Similarly, if one or more of the males died during an airborne-trapping run, the constituents of the metathoracic scent gland secretion appeared in the sample, and compounds 6-10 were more or less reduced in abundance depending on when the males died. When mature males were coaxed into the airborne-trapping apparatus without causing them to emit their metathoracic scent gland secretion and when none died during trapping, they released predominantly compounds eluting from 8-11 minutes (FIG. 2C). Males began releasing compounds 6-10 about one week after emergence to the adult. Airborne-trapped samples of mature virgin females contained constituents of the metathoracic scent gland secretion if they emitted the secretion during loading or if one or more died during trapping, but compounds 6-10 were always absent.

Identification of the Compounds in the Insect Volatiles.

Instrumentation. Electron impact (EI) and $NH_3$ chemical ionization (CI) mass spectra were collected using a Finnigan 4510 GC-MS as described by Aldrich et al., Arch. Insect Biochem. Physiol. 3: 1–12 (1986). $^1$H-NMR spectra were obtained at 60 MHz using a JEOL FX60Q FT instrument, and infrared spectra were obtained in a KBr pellet using a Perkin-Elmer 580B IR spectrometer.

Identification of Stink Gland Compounds. Compounds 1-5 (FIG. 2) (1, (E)-2-hexenal; 2, n-dodecane; 3, (E)-2-decenal; 4, n-tridecane; 5, (E)-2-decenyl acetate) were identified by GC-MS data and GC-coinjection with known standards of the identified compounds.

Identification of Male-Specific Volatiles.

A. Identification of the Novel Compounds of the Invention. Published EI-MS matching the spectra for compound 8 (trans-(Z)-α-bisabolene epoxide) and compound 9 (cis-(Z)-α-bisabolene epoxide) could not be found. The similarity of the EI-MS for these two natural products suggested that the compounds were isomers, and their MW=220 as determined by CI-MS indicated they were probably mono-oxegenated sesquiterpenes. Approximately 200 μg of 8 and 9 GC-trapped together produced a 60 MHz $^1$H-NMR spectrum that was apparently not complicated by the coexistence of two compounds, further suggesting that the compounds were isomers both having the (Z)-configuration. The $CDCl_3$ $^1$H-NMR spectrum of compounds 8 and 9 corresponded to the $^1$H-NMR spectrum of (Z)-α-bisabolene, except that the resonance for the cyclic olefinic proton of C-2 at 5.49 ppm was replaced by a one proton resonance at 3.08 ppm and one methyl group resonance was shifted upfield to 1.33 ppm. The $C_6D_6$ $^1$H-NMR spectrum of compounds 8 and 9 was similar to the $CDCl_3$ $^1$H-NMR spectrum of the compounds, except that the single proton resonance was shifted upfield by 0.81 ppm. A similar solvent-dependent upfield shift has been observed in the $^1$H-NMR spectra of bisabolene derivatives containing an epoxide group on the ring, and we confirmed this effect on our NMR instrument using a synthetic epoxide of oleic acid. Therefore, we suspected that compounds 8 and 9 were identical to compound 6, but with a C-1,2 epoxide moiety.

Figure 1:
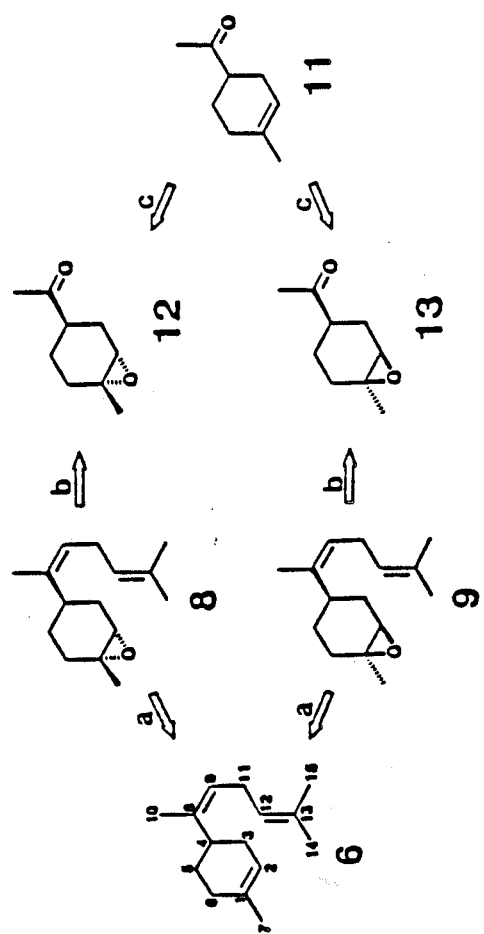
FIG. 1 illustrates the scheme for identification of the compounds; a is Zn, NaI, HOAc, NaOAc; b is $O_3$, and c is m-chloroperoxybenzoic acid.

Compounds 8 and 9 were deoxygenated after the procedure of Delay and Ohloff, supra. These compounds dexoygenated (FIG. 1) individually or as a mixture, produced a single new compound that coeluted with 6 and matched the MS of synthetic 6. Isolated components in ca. 100 μl of $CH_2Cl_2$ were ozonized by addition of 100 μl of $O_3$-saturated $CH_2Cl_2$ at −78° C. (8341 Matheson Laboratory Ozonator), and ozonides were cleaved with methyl sulfide (30 μl; 40 μl/μl $CH_2Cl_2$). Compounds 12 and 13 (1-methyl-4-acetyl-1,2-epoxycyclohexane) were synthesized by standard methods and structurally verified by spectral comparisons to published values for these isomers. Ozonolysis of compounds 8 and 9 together produced ozonides 12 and 13 (FIG. 1) in approximately the same ratio as the ratio of 8:9 in airborne-trapped samples. Thus, compound 8 is trans-(Z)-1-methyl-4-(1,5-dimethyl-1,4-hexadienyl)-1,2-epoxycyclohexane. Deoxygenation of isolated 9 (>80% purity) produced a single compound having a GC-retention time and MS identical to synthetic 6 (FIG. 1). Ozonolysis of isolated 9 produced 13, but did not produce 12. Thus, component 9 is cis-(Z)-1-methyl-4-(1,5-dimethyl-1,4-hexadienyl)-1,2-epoxycyclohexane.

B. Identification of Compounds 6, 7 and 10. The EI-MS of compounds 7 and 10 (FIG. 2) matched published spectra for nerolidol and n-nonadecane, respectively, and the CI-MS indicated the MW for the natural products were correct for these structural assignments. Compound 10 matched the GC retention time of authentic n-nonadecane (Aldrich Chemical Co.), and the GC retention time of compound 7 matched that for the E-isomer of nerolidol (3,7,11-trimethyl-1,6,10-dodecatriene-3-ol, Fritzsche Brother, Inc.).

The EI-MS and infrared spectrum of compound 6 matched the published spectra of α-bisabolene (FIG. 1), and the CI-MS verified that the natural product has a MW=204, as does α-bisabolene. Approximately 200 µg of 6 was isolated in pure form for $^1$H-NMR analysis. The NMR spectrum suggested the (Z)-configuration for the $C_{8,9}$ double bond (FIG. 1), and compound 6 coeluted with synthetic (Z)-α-bisabolene [synthetic standards of (E)- and (Z)-α-bisabolene supplied Dr. F. Delay, Firmenich SA, Geneva, Switzerland, were baseline-separated on packed capillary GC columns].

A mature male can release about 9 µg of compounds 6, 8, and 9 per day. The proportions of the male-specific volatiles (± standard error of the mean) were calculated based on GC-peak area integrations from 10 airborne samples, all of which contained <5% n-tridecane (the major stink gland component), as follows: 16.8 ±0.7% (Z)-α-bisabolene; 1.4±0.2% (E)-nerolidol; 43.9 ±1.4% trans-(Z)-α-bisabolene epoxide; 14.5±0.7% cis-(Z)-α-bisabolene epoxide, and 7.4±1.4% n-nonadecane. Tridecane concentrations in these samples ranged from 0.155 to 4.6% (2.3±0.5%), suggesting that this hydrocarbon is not a component of the male-specific blend.

Example 2

Synthesis of the Novel Compounds.

General. All reactions were carried out under argon atmosphere with dry freshly distilled solvents under anhydrous conditions unless otherwise noted. Ethereal solvents were dried and distilled under nitrogen from sodium benzophenone ketyl. Methylene chloride was distilled under nitrogen from calcium hydride. Amines were distilled under argon from calcium hydride. Reaction temperatures were externally measured.

Figure 4A:
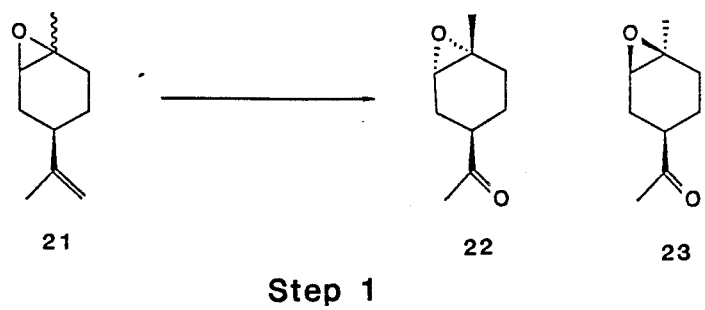
FIGS. 4A and 4B shows the steps for the synthesis of the R-cis compound.
Figure 4A:
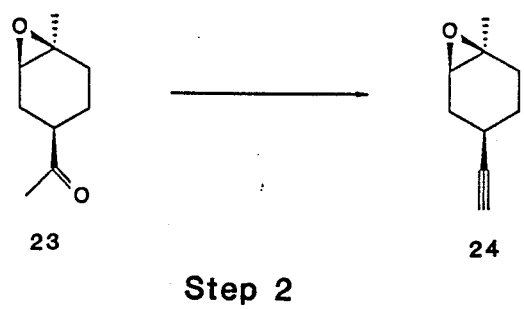
Figure 4A:
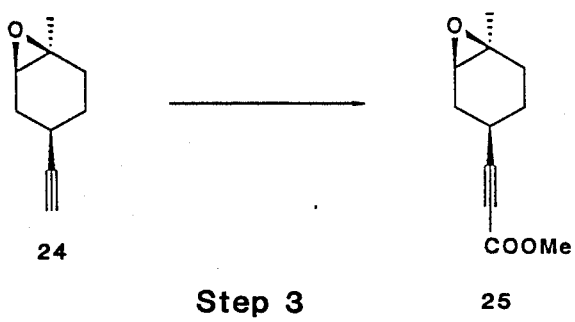
Figure 4A:
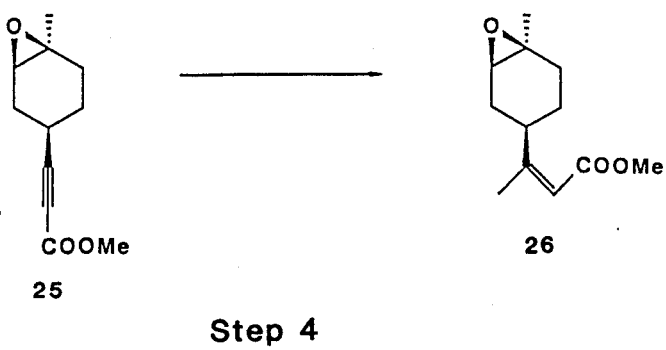
Figure 4B:
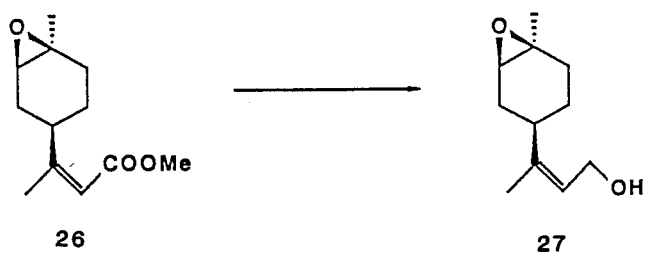
Figure 4B:
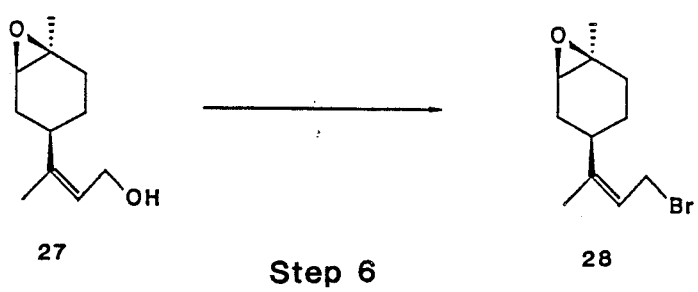
Figure 4B:
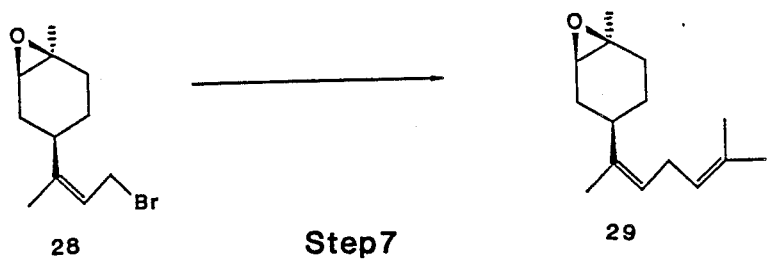

The R-cis, R-trans, S-cis, and S-trans compounds are shown in FIG. 3. The steps for synthesis of the compounds with reference to the R-cis compound are shown in FIGS. 4A and 4B and described in detail below.

Step 1. R-(+)-Limonene oxide (31 ml, 0.195 mole), 21, [purchased from Aldrich Chemical Co. (97%, mixture of cis- and trans- epoxides, ca. 1:1)], was dissolved in methylene chloride (500 ml) in a 2 l two necked flask with septum, magnetic stir bar, and 3-way stopcock. The solution was cooled to −78° C. (dry ice/acetone). Ozone was bubbled through the solution until a blue color persisted at which time an additional 250 ml of $CH_2Cl_2$ was added. To the diluted mixture was added triphenylphosphine (122 g, 0.4651 mole), and the reaction was allowed to warm to room temperature over six hours. The solvent was evaporated by rotary evaporation, and the residue taken up in ether. The crystallized triphenylphosphine oxide was filtered off through silica, and the filtrate concentrated to a thin yellow oil. Flash column chromotrography (FCC) using gradient elution, 5%, 10%, 15%, 20%, 30%, 40%, ether-petroleum ether furnished about 1:1:1 ratio of pure 22, pure 23, and a mixture of the two in 82% overall yield. The mixture was resubjected to FCC to separate the diastereomers.

Step 2. The methyl ketone, 23, was converted to the terminal acetylene, 24, using the procedure of Negishi et al., supra. In a flame-dried 100 ml flask with stir bar and 3-way stopcock, lithium diisopropylamide (LDA) was made at 0° C. under standard conditions (14.5 ml THF, 2.2 ml diisopropylamine distilled from $CaH_2$, and 10.5 ml of a 1.5 M solution of n-BuLi in hexanes). After stirring the LDA at 0° C. for 0.5 hour, it was cooled to −78° C., then 23 was added via cannula in 5 ml of THF over ca. 5 minutes, and the resultant mixture stirred at −78° C. for 1 hour. Diethylchlorophosphate (2.3 ml, 0.0159 mole) was then added via syringe. After warming the brown reaction mixture to room temperature over 3.5 hours, it was added to a −78° C. solution of LDA made at 0° C. under standard conditions (39 ml THF, 5.5 ml diisopropylamine, 26 ml of a 1.5M solution n-BuLi in hexanes) over 1.5 hours via cannula. The reaction mixture was allowed to warm to 0° C. over 3 hours at which time it was quenched by addition of 50 ml of a saturated (sat.) solution of $NH_4Cl$. The aqueous solution was extracted 3×50 ml hexanes. The combined organic extracts were washed with 3×20 ml 1N HCl, 1×20 ml sat. $NaHCO_3$, 1×20 ml brine, dried with $MgSO_4$, filtered and concentrated to give a volatile clear, colorless oil. FCC of the crude product yielded 24, 1.15 g (8.44 mmole), 60% yield, of the product, having a light sweet piney odor.

Step 3. THF (500 ml) was added to the terminal acetylene, 24, (16.78 g, 0.123 mole) and cooled to −78° C. n-BuLi (1.6M solution in hexanes) was added via syringe, and the solution stirred for 1 hour. Methyl chloroformate (distilled from $CaH_2$, 8.9 ml, 0.1148 mole) was added via syringe, and the reaction allowed to warm to room temperature over 2 hours. The reaction was diluted with ethyl acetate (EtOAc), 500 ml, after quenching with excess methanol, and washed with $H_2O$, 2×150 ml, and brine, 1×150 ml. The organic solution was dried over $MgSO_4$, filtered and concentrated giving a slightly yellow oil. A clear, colorless oil, 25, was obtained in 92% yield (19.48 g, 0.1003 mole) after FCC, 10% ether-pet. ether.

Step 4. The double bond was stereoselectively introduced using the procedure of E. J. Corey et al., supra. A 50 ml flask with stir bar and 3-way stopcock was flame dried and cooled under argon. Copper iodide (0.720 g, 3.78 mmole) was then added followed by THF (18 ml). The resultant gray slurry was cooled to 0° C. and methyllithium (1.4M solution in ether, ca. 5.6 ml) was added via syringe until the solution became clear and colorless. After stirring for 15 minutes at 0° C., the reaction was cooled to −78° C. at which time the α,β-acetylenic ester, 25, (0.6994 g, 3.60 mmole) was added in 5 ml of THF via cannula dropwise over ca. 3 minutes. The resultant turbid yellow solution was stirred at −78° C. for 3 hours. Excess methanol was added to quench the reaction, and the cooling bath was removed. Once the reaction reached room temperature, it was poured into a saturated solution of $NH_4Cl$ (50 ml) in a separatory funnel and shaken until the solution of turned blue. The mixture was then extracted with 3×25 ml $CH_2Cl_2$. The combined organic layers were dried over $MgSO_4$, filtered, and the solvent evaporated giving a slightly yellow oil. FCC of the crude product (10% ether-pet. ether) yielded the product, 26, as a clear colorless oil (0.6545 g, 3.113 mmole) in 86.4% yield. Only one double bond isomer was detected.

Step 5. The α,β-unsaturated ester, 26, (2.129 g., 0.01012 mole) was reduced in a 1,2-fashion by addition of diisobutylaluminum hydride (DIBAL), (1.0M solution in $CH_2Cl_2$, 25.3 ml) to a cold ($-78°$ C.) solution of the ester in THF (67 ml). The reaction was quenched at $-78°$ C. with the addition of a large excess of methanol after stirring for 3 hours at $-78°$ C. Dilution with EtOAc (150 ml) followed after removal of the cold bath and warming of the reaction to room temperature. The organic solution was then washed with 6×50 ml sat. Rochelle's salt and 1×50 ml brine. Drying over $MgSO_4$, filtration, and finally evaporation of the solvent yielded a clear, colorless oil which was subjected to FCC (60% ether-pet. ether). The product, 27, was obtained in 87% yield (1.587 g., 8.706 mmole). THF is necessary as the solvent otherwise epoxide opened products are obtained in great preponderance. DIBAL as a solution in $CH_2Cl_2$ was more effective that DIBAL in either THF or hexanes solutions.

Step 6. Methylene chloride (2.4 ml) was added to the allylic alcohol, 27, (88.9 mg, 0.4878 mmole) via syringe followed by carbon tetrabromide (0.2150 g, 0.6843 mmole), and the mixture cooled to $-23°$ C. ($CCl_4$/dry ice). Triphenylphosphine (0.157 g, 0.5986 mmole) was then added as a solution in 1 ml $CH_2Cl_2$ via cannula. The resultant yellow solution was stirred at $-23°$ C. for 15 minutes after which it was diluted with pet. ether. Quick filtration through a pad of silica gel and evaporation of the solvent yielded a slightly yellow oil. Purification by FCC 10% ether-pet. ether gave the unstable allylic bromide, 28, (75.6 g, 0.3084 mmole, 63% yield) as a clear, colorless oil which turned yellow upon standing at room temperature.

It should be noted that preliminary results with regards to the conversion of the allylic alcohol, 27, to the allylic chloride, rather than allylic bromide, indicate that the allylic chloride is more stable and the yields for the synthesis of this compound are greater than for that of the bromide.

Step 7. A 10 ml flask with 3-way stopcock and magnetic stir bar was flame dried and cooled under argon and then was charged with THF (1.0 ml) and cooled to $-78°$ C. t-Butyllithium (2.0M solution in pentane, 0.33 ml, 0.66 mmole) was added to the solvent giving a yellow solution. To the yellow solution was added 1-bromo-2-methyl propene (0.034 ml, 0.33 mmole) giving a colorless solution, indicating the formation of the vinyl lithium species, after stirring at $-78°$ C. for 2.5 hours. The allylic bromide, 28, (74.3 mg, 0.303 mmole) in THF (0.5 ml) was added as a solution to the vinyl anion of 1-bromo-2-methyl propene via cannula with 2×0.5 ml THF washings of the flask also being added. The reaction was quenched with the addition of water after stirring for 10 minutes at $-78°$ C. and then warmed to room temperature. After diluting with hexanes (15 ml), the organic layer was washed with 2×5.0 ml water and 1×5.0 ml brine. FCC (5% ether-pet. ether) of the residue from the evaporation of the solvent gave 54.1 mg (0.2455 mmole, 81% yield) of the R-cis product, 29, as a clear, colorless oil.

The synthesis of the R-trans product is the same as described above except that the R-trans-methyl ketone, 23, is used in step 2. The same reaction conditions were utilized with very similar yields being obtained.

Figure 5:
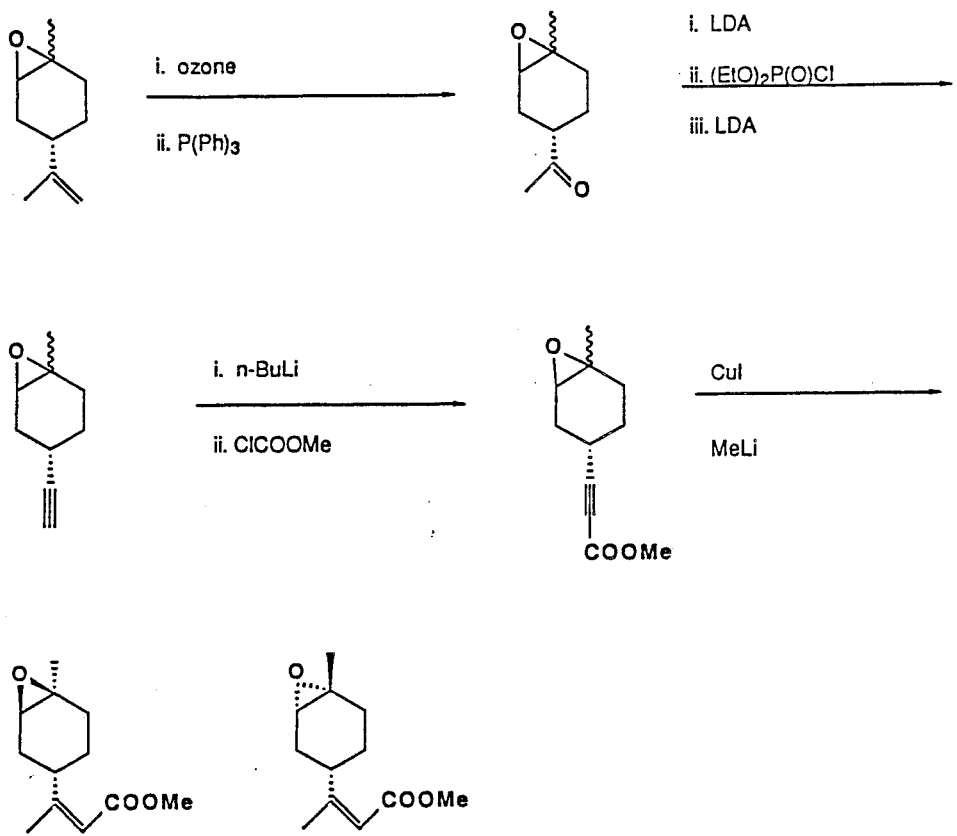
FIG. 5 shows an alternate synthetic scheme for preparing the compounds.

During the synthesis of the R-cis and R-trans products, it was discovered that the α,β-unsaturated esters were much more easily separated by FCC using gradient elution, 5%, 10%, 15%, 20%, 25% ether-pet. ether than the methyl ketones, i.e., 22 and 23. Therefore in the synthesis of the S-cis and S-trans products, the two diasteromers were separated as the α,β-unsaturated esters. The synthesis of the unsaturated esters is outlined in FIG. 5. The pure esters were then converted, as was compound 26 to 29, to the final products using the same reaction conditions with similar yields. The starting material for the S-cis and trans series was S-(−)-limonene oxide, 97%, ca. 1:1 mixture of cis- and trans-epoxides. Where a racemic mixture is desired as the product, then racemic limonene oxide is used as the starting material.

Comparison of the Synthetic and Insect-Derived Compounds. The EI-MS and GC-retention times of synthetic trans- and cis-(Z)-epoxides were identical to those of insect-derived compounds 8 and 9, respectively. In addition, the 500 MHz $^1$H-NMR spectra of synthetic trans- and cis-(Z)-epoxides matched the spectra for insect-derived compounds 8 and 9, respectively, except for the presence of a signal at 0.4 ppm in the insect samples due to methylsilicone contamination from GC column bleed during trapping.

It is understood that the foregoing detailed description is given merely by way of illustration and that modification and variations may be made within, without departing from the spirit and scope of the invention.

We claim:

1. The pure or substantially pure compound trans-(Z)-1-methyl-4-(1,5-dimethyl-1,4-hexadienyl)-1,2-epoxycyclohexane.

2. The pure or substantially pure compound cis-(Z)-1-methyl-4-(1,5-dimethyl-1,4-hexadienyl)-1,2-expoxycyclohexane.

3. A mixture comprising the pure or substantially pure compound trans-(Z)-1-methyl-4-(1,5-dimethyl-1,4-hexadienyl)-1,2-epoxycyclohexane in combination with the pure or substantially pure compound cis-(Z)-1-methyl-4-(1,5-dimethyl-1,4-hexadienyl)-1,2-expoxycyclohexane.

4. The compound of claim 1 which is in the R- or S-configuration.

5. The compound of claim 2 which is in the R- or S-configuration.

6. A method of preparing a compound selected from the group consisting of R-cis-, R-trans-, S-cis-, and S-trans-(Z)-1-methyl-4-(1,5-dimethyl-1,4-hexadienyl)-1,2-epoxycyclohexane, which comprises:

(1) ozonating R-(+)-limonene oxide or S-(−)-limonene oxide to form about a 1:1 mixture of cis and trans ozonides and decomposing said ozonides to obtain a mixture of cis and trans methyl ketones, and separating said cis and trans methyl ketones;

(2) converting said cis or trans methyl ketone to a terminal acetylene;

(3) acylating said terminal acetylene to obtain a α,β-acetylenic ester;

(4) stereoselectively converting said α,β-acetylenic ester to a (Z)-α,β-unsaturated ester;

(5) reducing said (Z)-α,β-unsaturated ester to an allylic alcohol;

(6) converting said allylic alcohol to an allylic halide; and (7) adding a vinyl anion to said allylic halide to obtain a compound selected from the group consisting of R-cis-, R-trans-, S-cis-, and S-trans-(Z)-1-methyl-4-

(1,5-dimethyl-1,4-hexadienyl)-1,2-epoxycyclohexane, wherein if said starting material in step 1 is R-(+)-limonene oxide, said compound in step 7 is in the R configuration, and wherein if said starting material in step 1 is S-(−)-limonene oxide, said compound in step 7 is in the S configuration.

7. The method of claim 6 wherein steps 1 through 4 are replaced with the following steps:

(1) ozonating R-(+)-limonene oxide or S-(−)-limonene oxide to form about a 1:1 mixture of cis and trans ozonides and decomposing said ozonides to obtain a mixture of cis and trans methyl ketones;

(2) converting said cis and trans methyl ketones to cis and trans terminal acetylenes;

(3) acylating said terminal acetylenes to obtain cis and trans $\alpha,\beta$-acetylenic esters;

(4) stereoselectively converting said $\alpha,\beta$-acetylenic esters to cis and trans (Z)-$\alpha,\beta$-unsaturated esters, and separating said cis and trans (Z)-$\alpha,\beta$-unsaturated esters.

* * * * *